United States Patent [19]

Carl et al.

[11] 4,423,249

[45] Dec. 27, 1983

[54] PREPARATION OF HALOFLUOROALKYL ETHERS

[75] Inventors: William P. Carl, Angleton; Bobby R. Ezzell, Lake Jackson, both of Tex.

[73] Assignee: The Dow Chemical Company, Midland, Mich.

[21] Appl. No.: 296,607

[22] Filed: Aug. 26, 1981

[51] Int. Cl.$^3$ .............................................. C07C 41/16
[52] U.S. Cl. .................................... 568/655; 568/683; 568/669; 568/684; 568/685
[58] Field of Search ................ 568/684, 655, 683, 669

[56] References Cited

U.S. PATENT DOCUMENTS 3,926,989 12/1975 Rebsdat et al. ................. 568/655 X
4,377,711 3/1983 Rico et al. ....................... 568/655 X

OTHER PUBLICATIONS

Tarrant et al., J.A.C.S., vol. 75 (1953) 932–934.
Corley et al., J.A.C.S., vol. 78 (1956) 3489–3493.
Scipioni et al., (English Translation) Ann. Chim. Rome, 57(7) (1967) 817–824.
Banus et al., J. Chem. Soc. (1951) 60–64.

*Primary Examiner*—Bernard Helfin
*Attorney, Agent, or Firm*—Paul D. Hayhurst

[57] ABSTRACT

Alkyl or aryl 1,1-difluoroalkyl ethers, e.g., 1,1,2-trifluoro-2-chloro-2-iodoethyl phenyl ether, are prepared by reacting an alkoxide or phenoxide with a 1,1-difluoro-1,2-dihaloethane (with the proviso that halo is not fluoro and at least one of the halo substituents is bromo or iodo) in an organic solvent at temperatures ranging from about $-30°$ C. to about $100°$ C. These compounds may be dehalogenated with zinc to form the corresponding vinyl ethers.

The reaction of halogen derivatives of fluorocarbons with nucleophiles is dramatically facilitated by a bromo or iodo substituent in the beta position.

11 Claims, No Drawings

PREPARATION OF HALOFLUOROALKYL ETHERS

BACKGROUND OF THE INVENTION

This invention relates to a method for the preparation of alkyl or aryl halofluoroalkyl ethers.

Traditionally, dihydrocarbyl ethers such as arylalkyl ethers are prepared by the Williamson synthesis. In the Williamson synthesis, an alkyl halide or substituted alkyl halide is reacted with a sodium alkoxide or a sodium phenoxide to form the corresponding alkyl ether or aryl alkyl ether. The Williamson synthesis simply involves nucleophilic substitution of an alkoxide ion or a phenoxide ion for a halide ion.

Nucleophilic displacement of halogen ions from alkyl halides is a well-known reaction and displacement proceeds in the order $F<<Cl<Br<I$. Halogens on carbons beta to the reaction site usually retard the displacement. R. D. Chambers, *Fluorine in Organic Chemistry*, at 98 (1973). On the other hand, perfluoroalkanes and some of their chloro derivatives and to a lesser extent, bromo derivatives, are extremely resistant to nucleophilic attack.

W. J. Pummer and L. A. Wall, in the July 1963 *SPE Transactions*, have reported on the synthesis of 1,2,2,-trifluorovinyl phenyl ether and 1,2,2-trifluorovinyl perfluorophenyl ether in studies of high temperature polymers. Two methods were discussed. First, 1,1,2,2-tetrafluoroethyl phenyl ether was formed by reaction of phenoxide with tetrafluoroethylene and was then dehydrofluorinated under a variety of conditions. Formation of the desired vinyl ether was poor, usually resulting in yields of 5 percent or less. The second method was the reaction of phenoxide with tetrafluoroethylene under extremely anhydrous conditions. This was found to be the preferred method using mixed solvents, but yields still did not exceed 35 percent even under the best conditions.

In view of the aforementioned deficiencies of currently known techniques for making certain fluorovinyl phenyl ethers and their precursors, it is highly desirable to provide a method for preparing such precursors in yields greater than 35 percent.

SUMMARY OF THE INVENTION

In one aspect, this invention is such a method that comprises contacting in a solvent a 1,2-dihalo-fluorohydrocarbon with a metal hydrocarboxide under conditions such that an ether of the hydrocarboxide and the fluorohydrocarbon is formed. Substitution of iodine or bromine on the beta carbon to α-chloro-fluorocarbons results in replacement of the α-chlorine with the hydrocarboxide under mild conditions, a reaction that is known to be difficult. Particularly surprising is the fact that chloride is replaced preferentially to iodide or bromide. Another surprising feature of the present invention is the formation of little or no diether.

The products produced from the reaction are useful chemical intermediates and undergo a variety of reactions typical of fluorocarbon halides. Of special interest is the production of alkyl or aryl vinyl ethers by reaction of the products with known dehalogenation reagents. Exemplary of this is the reaction of zinc with 2-bromotetrafluoroethyl phenyl ether to produce phenyl trifluorovinyl ether, a compound difficult to prepare otherwise.

DETAILED DESCRIPTION OF THE INVENTION

Generally, the 1,2-dihalo fluorohydrocarbons of this invention are represented by formula I:

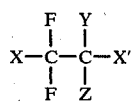

wherein X is selected from the group consisting of Cl, Br and I; X' is selected from the group consisting of Br and I; and Y and Z are independently selected from the group consisting of H, F, Cl, Br, I and R', wherein R' is selected from the group consisting of aryl, alkyl including cycloalkyl, or substituted alkyl with the proviso that R' does not interfere with the reaction between the hydrocarboxide and the compound of formula I; under conditions sufficient to form an ether represented by formula II

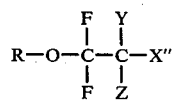

wherein Y and Z are as previously described; X" is selected from the group consisting of Br, I and H; and R is aryl or alkyl with the proviso that the carbon of said alkyl which is bonded to the oxygen atom shown in formula II must not have any fluorine substituent.

For the purposes of this invention, alkyl and aryl include substituted alkyl and aryl, except that when R is an alkyl moiety the carbon of said alkyl which is bonded to the oxygen atom shown in formula II must not have any fluorine substituent, and with the further limitation that any substituent on the alkyl or aryl moieties must not interfere with the disclosed inventive reaction.

The metal hydrocarboxide is typically a metal salt of an alcohol or phenol, thus the hydrocarboxide is typically an alkoxide or phenoxide. The metal salt may be represented by the formula ROM, where M is metal and R is as described hereinbefore. Preferably, R is phenyl. M is preferably an alkali metal or an alkaline earth metal, most preferably M is potassium or sodium. Generally, from about 0.1 to about 10.0 moles of metal hydrocarboxide is supplied per mole of halofluorohydrocarbon to be reacted. Preferably, from about 0.75 to about 1.1 moles of metal hydrocarboxide is supplied per mole of halofluorohydrocarbon.

These reactions can be conducted in a wide range of aprotic solvents when the iodo- or bromo-substituted product is desired. Representative of these solvents are glyme, tetraglyme, diglyme, triglyme, dioxane, tetrahydrofuran, dimethylformamide, acetonitrile and the like. In general, it is preferable that the solvent be chosen as a relatively polar aprotic type. The aprotic requirement is not rigid when hydrogen-substituted products are desired. Even then, it is more convenient to use an aprotic solvent and introduce controlled amounts of protic materials. When iodo-substituted reactants are used, the preferred solvent is tetraglyme. Use of solvents such as tetrahydrofuran or dioxane leads to some diether formation. The most critical reaction condition is that when the iodo- or bromo-substituted products are desired in high yield to the exclusion of hydrogen-substituted products protic materials such as water, alcohols or phenols, should be substantially excluded. Preferably, the reaction mixture will contain less than 0.1 percent protic materials. Most preferably, the reaction mixture will contain no detectable protic materials.

The solvent is employed in amounts such that the metal hydrocarboxide and the fluorohydrocarbon are homogeneously dispersed. Preferably, from about 0.5 to about 4.0 moles of solvent are employed per mole of metal hydrocarboxide. Most preferably, from about 1.5 to about 2.5 moles of solvent are employed per mole of metal hydrocarboxide.

The temperature and pressure of the reactions is not particularly critical. The temperature can be varied from about $-30°$ C. up to about 100° C. when operating at atmospheric pressure. Extremely low temperatures simply slow the rate to undesirable times. Excessively high temperatures can lead to some by-product formation. Ambient conditions are preferred simply from a convenience standpoint. Preferably, the process is conducted between about 0° C. to about 25° C. when operating at atmospheric pressure. The reaction can be done at sub- or superatmospheric pressure. For convenience, it is normally carried out at atmospheric or only slightly higher pressures. The product may be recovered by conventional means such as distillation or extraction. The by-product metal halide may be recovered by conventional means such as centrifugation or filtration.

The present invention includes the discovery that the reaction of halogen derivatives of fluorocarbons with nucleophiles is dramatically facilitated by an iodo or bromo substituent in the beta position. Further, in some cases the halogen, such as chloro, known to be more difficult to displace is in reality preferentially replaced. This surprising discovery is demonstrated by the following reactions.

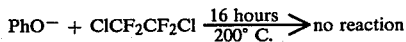  I

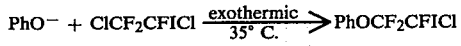  II

Ph = phenyl

Both reactions used tetraglyme as solvent. Reaction I is not surprising since chloro-substituted fluoroalkyls are known to be highly resistant to nucleophilic attack. Reaction II is indeed unexpected since chlorine is replaced exothermically from the same reaction center as is shown to be essentially inert even under the far harsher conditions of Reaction I. Clearly, substitution of iodine in the beta position has a marked effect on reactivity and one opposite to that known for hydrocarbons. Further, considering the known order of displacement of halogens by nucleophiles, it is even more surprising that chlorine rather than iodine is replaced.

Another surprising feature of the present invention is the lack of diether formation. This is demonstrated by the following reaction:

PhO$^-$ + BrCF$_2$CF$_2$Br → PhOCF$_2$CF$_2$Br    III

Under dry conditions, the reaction proceeds near quantitatively and exothermically to the mono-substituted product shown above. Clearly, substitution of the beta bromine by the ether group retards reactivity of the second bromine.

In addition to the halo-substituted products shown in reactions II and III, it is also possible to form hydrogen-substituted products. The presence of moisture or other protic materials in the reaction mixture results in at least partial replacement by hydrogen of the bromo or iodo substituent of the products. For instance, failing to thoroughly dry the phenoxide or using a mixture of phenol and phenoxide in Reaction III results in hydrogen-substituted products along with the halogen-substituted products.

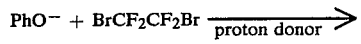

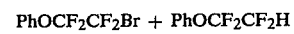

The relative amounts of hydrogen versus iodo- or bromo-substituted products can be controlled by controlling the amounts of protic materials present during the reaction.

The present invention represents a new synthetic tool useful in producing chemical intermediates otherwise difficult to prepare. The extremely high yields and mild reaction conditions mean that the reactions are extremely economical for producing the desired intermediates and thus any products formed from the intermediates.

The following are illustrative embodiments of this invention and comparative experiments. The examples should not be interpreted as limiting the scope of the invention. All parts and percentages are by weight unless otherwise indicated.

EXAMPLE 1

Reaction of potassium phenoxide with ClCF$_2$CFClI

Tetraglyme (200 ml) distilled from sodium, and 53 g of ClCF$_2$CFClI, are placed into a 3-neck vessel fitted with a thermometer, a stirrer and dropping funnel containing 50 ml of a 25 percent potassium phenoxide solution in tetraglyme. The phenoxide solution is added slowly to keep the temperature stable close to 35° C. The volatile materials are distilled out under vacuum and are analyzed by gas chromatograph and mass spectrometer. The products are resolved on a 6'×⅛" stainless steel column, which is packed with 20 percent Viton A on 80–100 mesh Celite, with nitrogen carrier gas at 20 ml/min and oven program of 60° C. for 4 minutes and then 16° C./min up to 220° C. Products and resolution times based on mass spectral data are shown in Table I:

TABLE I

| Resolution Time | Results of Example I | |
|---|---|---|
| | Product | Product Amount |
| 8.6 min | PhOCFClCF$_2$Cl | minor amount |
| 8.69 min | PhOCF$_2$CFHCl | approx. ⅓ of products |
| 11.09 min | PhOCF$_2$CFICl | approx. ⅔ of products |

COMPARATIVE EXPERIMENT 1

Reaction of potassium phenoxide with 1,2-dichlorotetrafluoroethane

Forty ml of a 25 percent solution of potassium phenoxide in tetraglyme is introduced into a 100 ml stainless steel container fitted with a manifold assembly including a rupture disc and pressure gauge. The reactor is evacuated, cooled to $-78°$ C. and 59.5 g of $ClCF_2CF_2Cl$ is condensed into the container. The reactor is then heated to 200° C. overnight, cooled, and the solution is injected into a gas chromatograph equipped with a mass spectrometer. The analysis shows 1,2-dichlorotetrafluoroethane, phenol and phenoxy hydrocarbon ethers demonstrating little or no reaction of the phenoxide with the fluoroalkyl chloride.

EXAMPLE 2

Reaction of potassium phenoxide with $BrCF_2CF_2Br$

Well purified potassium phenoxide (135 g) and 450 ml of tetraglyme at 0° C., distilled off of sodium, are added to a 3-neck flask equipped with a stirrer, thermometer and a dropping funnel. $BrCF_2CF_2Br$ (125 ml) is put in the funnel and 121.5 ml is added dropwise with stirring and cooling to hold the reaction temperature close to 10° C. Gas chromatograms of the completed addition reaction product show 97.9 percent conversion and essentially 100 percent yield based on $BrCF_2CF_2Br$.

EXAMPLE 3

1,2,2-Trifluorovinyl phenyl ether

Dried tetraglyme (750 ml) is used as a solvent in a 2 liter, 3-neck flask equipped with a stirrer, thermometer and dropping funnel. Four and one-half moles of PhOK are prepared in situ by adding 481 g PhOH and 415 g KOH and distilling off the water until a minimal phenolic peak is visible on the chromatogram.

Next, 359 ml of $BrCF_2CF_2Br$ is added dropwise with cooling to hold the temperature to 20° C. in the reactor. Following the addition, the reactor is continually stirred for 66 hours to allow evaluation of any change in distribution. The products do not change so the vessel is fitted with a packed Vigreaux column and stillhead followed by two series $-78°$ C. traps. The products are distilled out of the vessel under vacuum with heating applied by a mantle, gradually raising the temperature from ambient up to 120° C. Products (336 ml) are collected and identified using mass spectrometry. The chromatographic analysis shows the solution to contain 433 g of $PhOCF_2CF_2Br$, 47.7 g of $PhOCF_2CF_2H$, and 58.2 g of $BrCF_2CF_2Br$. This represents a yield of 57 percent of the bromo product based on 93 percent conversion of the $BrCF_2CF_2Br$.

The product solution is then added dropwise to 400 ml of tetraglyme and 130 g of HCl-washed zinc granules in a stirred 4-neck flask fitted with a heating mantle, dropping funnel, thermometer, stirrer and cold finger condenser with nitrogen pad through a bubble trap. The reactor is heated to 100° C. as addition begins. When the reaction initiates, the mantle is controlled along with the addition rate to keep the temperature at approximately 110° C. Following the completed addition, the reaction is kept at 110° C. with stirring for one hour. A chromatogram of the reaction mixture before distillation indicates 0.02 area percent is residual $BrCF_2CF_2Br$, 0.05 area percent is $FCF_2CF_2Br$, 50.2 area percent is $PhOCF=CF_2$, 5.96 area percent is $PhOCF_2CF_2H$, with a detectable trace of $PhOCF_2CF_2Br$, and the remainder tetraglyme and 3.45 area percent coupling products and vinyl ether dimers. Based on chromatographic sensitivity determinations, this constitutes a yield of 79.4 percent to the unsaturated product. The distillation yields 210 g of isolated $PhOCF=CF_2$ which is greater than 99 percent pure with the structure being confirmed by mass spectroscopy and $F^{19}$ NMR.

EXAMPLES 4-8

Reaction of potassium phenoxide with $ICF_2CF_2Br$

Twenty ml of one of five solvents and 3.49 g of $ICF_2CF_2Br$ are placed into five 75 ml stainless steel reactors which are then plugged and cooled to $<-20°$ C. While cooled, the reactors are taken into a dry box, unplugged and 3.58 g of PhOK is added. The reactors are then fitted with a manifold assembly composed of a tee with pressure gauge, valve and rupture disc. The reactors are placed on a shaker at ambient temperature and are removed for analysis after 16 hours. The chromatograms of the different reactor solutions show the product percentages to be as indicated in Table II.

TABLE II

Results of Examples 4-8
Products as a Function of Solvent (Wt %)

| Solvent | Compound[1] | Compound[2] | Compound[3] | Di-ether | Other High MW |
|---|---|---|---|---|---|
| Tetraglyme | 6.74 | 68.65 | 21.48 | 0 | 3.13 |
| Diglyme | 3.09 | 77.27 | 19.64 | 0 | 0 |
| Glyme | 1.46 | 39.91 | 50.87 | 7.76 | 0 |
| THF | 10.68 | 15.80 | 48.81 | 24.08 | 0.63 |
| Dioxane | 1.01 | 4.61 | 41.39 | 37.80 | 15.19 |

[1] $PhOCF_2CF_2H$
[2] $PhOCF_2CF_2Br$
[3] $PhOCF_2CF_2I$

The use of diglyme most enchances the formation of the brominated ether, while the use of glyme best promotes iodo ether formation. The use of tetrahydrofuran (THF) also results in a high yield of the iodo ether, however, large amounts of the diether and the hydrogen-substituted ether are also formed. The largest amount of diether is formed when dioxane is the solvent.

EXAMPLES 9-12

Reaction of potassium phenoxide with $ICF_2CF_2I$

Five 75 ml stainless steel reactors are each loaded with 20 ml of one of five solvents and 3.7 ml of $ICF_2CF_2I$, plugged, then cooled to $<-20°$ C. The reactors are then put into a dry box and 3.58 g PhOK is added. The reactors are then fitted with a manifold assembly composed of a tee with pressure gauge, valve and rupture disc. The reactors are placed on a shaker at ambient temperature overnight. The solutions are analyzed by chromatograph and show the product percentages indicated in Table III.

TABLE III

Results of Experiments 9-12
Products as a Function of Solvent (Wt %)

| Solvent | $PhOCF_2CF_2H$ | $PhOCF_2CF_2I$ | Di-ether | Other High MW |
|---|---|---|---|---|
| Tetraglyme | 14.26 | 76.02 | 0 | 9.72 |
| Diglyme | 7.63 | 68.18 | 0 | 24.19 |
| Glyme | 3.38 | 95.39 | 0 | 1.23 |
| THF | 15.16 | 53.51 | 28.28 | 3.05 |

The use of glyme solvent produces excellent results. Tetraglyme and diglyme solvents give good results with no diether formation, but THF produces a high amount of the diethers.

EXAMPLE 13

Reaction of CH₃ONa with BrCF₂CF₂Br

Well dried glyme (325 ml) and 27 g of well dried sodium methylate are added to a 3-neck reactor equipped with dropping funnel, thermometer, cold finger condenser and magnetic stirrer. A nitrogen pad with a bubble trap is used. Sixty ml of BrCF₂CF₂Br is then added at 30° C. The reactor is cooled to 20° C. and a chromatogram shows CH₃OCF₂CF₂Br is produced. Analysis by gas chromatograph-mass spectrometer shows the lower boiling materials to be BrCF₂CF₂Br and CH₃OCF₂CF₂Br when eluted through 6 feet of ⅛ inch stainless steel column using N₂ carrier gas at 20 ml/min and temperature program of 4 min at 50° C. and 16° C./min up to 220° C. The BrCF₂CF₂Br elutes at 0.64 min and the BrCF₂CF₂OCH₃ elutes at 0.97 min.

What is claimed is:

1. A process comprising contacting in an aprotic solvent a metal hydrocarboxide with a halofluoroalkyl compound represented by formula I

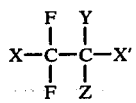
    I wherein X is selected from the group consisting of Cl, Br and I; X' is selected from the group consisting of Br and I; and Y and Z are independently selected from the group consisting of F, Cl, Br, I and R', wherein R' is selected from the group consisting aryl, alkyl including cycloalkyl, or substituted alkyl with the proviso that R' does not interfere with the reaction between the metal hydrocarboxide and the compound of formula I; under conditions sufficient to form an ether represented by formula II

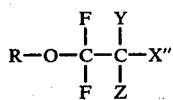
    II wherein Y and Z are as previously described; X" is selected form the group consisting of Br, I and H; and R is aryl or alkyl with the proviso that the carbon of said alkyl which is bonded to the oxygen atom shown in formula II must not have any fluorine substituent.

2. The process of claim 1 wherein the metal hydrocarboxide is a metal salt of an alcohol or phenol, said metal salt being represented by formula III

   R—O—M    III wherein M is a metal.

3. A process comprising contacting in an aprotic solvent and in a reaction system from which water or protic materials are substantially excluded a metal hydrocarboxide, which is a metal salt or an alcohol or phenol, said metal salt being represented by the formula R—O—M wherein M is a metal and R is aryl or alkyl with the proviso that the carbon of said alkyl which is bonded to the oxygen atom shown in formula II must not have any fluorine substituent, with a halofluoroalkyl compound represented by formula I

    I wherein X is selected from the group consisting of Cl, Br and I; X' is selected from the group consisting of Br and I; and Y and Z are independently selected from the group consisting of F, Cl, Br, I and R', wherein R' is selected from the group consisting of aryl, alkyl including cycloalkyl, or substituted alkyl with the proviso that R' does not interfere with the reaction between the metal hydrocarboxide and the compound of formula I; under conditions sufficient to form an ether represented by formula II

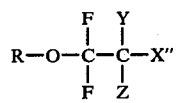
    II wherein R, Y and Z are as previously described, and X" is selected from the group consisting of Br, and I.

4. A process comprising contacting at a temperature between about −30° C. up to about 100° C. in the presence of an aprotic solvent and in a reaction system from which water or protic materials are substantially excluded, a metal hydrocarboxide, which is a metal salt of an alcohol or phenol, said metal salt being represented by the formula R—O—M wherein M is a metal and R is aryl or alkyl with the proviso that the carbon of said alkyl which is bonded to the oxygen atom shown in formula II must not have any fluorine substituent, with a halofluoroalkyl compound represented by formula I

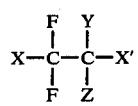
    I wherein X is selected from the group consisting of Cl, Br and I; X' is selected from the group consisting of Br and I; and Y and Z are independently selected from the group consisting of F, Cl, Br, I and R', wherein R' is selected from the group consisting of aryl, alkyl including cycloalkyl, or substituted alkyl with the proviso that R' does not interfere with the reaction between the metal hydrocarboxide and the compound of formula I; under conditions sufficient to form an ether represented by formula II

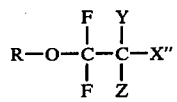
    II wherein R, Y and Z are as previously described, and X" is selected from the group consisting of Br and I.

5. The process of claim 4 wherein Y and Z are independently selected from the group consisting of F, Cl and R'.

6. The process of claim 5 wherein M is selected from the group consisting of alkali metals and alkaline earth metals.

7. The process of claim 6 wherein the solvent is selected from the group consisting of glyme, diglyme, triglyme, tetraglyme, dimethylformamide and acetonitrile.

8. The process of claim 7 wherein the process is conducted at a temperature between about 0° C. and 25° C. at atmospheric pressure.

9. The process of claim 8 wherein R is benzene and M is sodium or potassium.

10. The process of claim 9 wherein Y and Z are F, and X and X' are independently selected from the group consisting of Br and I.

11. The process of claim 10 wherein X, X' and X'' are Br, Y and Z are F, and the solvent is tetraglyme.

* * * * *

UNITED STATES PATENT AND TRADEMARK OFFICE
CERTIFICATE OF CORRECTION

PATENT NO. : 4,423,249

DATED : December 27, 1983

INVENTOR(S) : William P. Carl and Bobby R. Ezzell

It is certified that error appears in the above—identified patent and that said Letters Patent is hereby corrected as shown below:

Column 2, line 15, "consisting of H,F,Cl,Br,I and R'," should read -- consisting of F,Cl,Br,I and R', --.

Column 6, line 3, "with $ICF_2CF_{Br}$" should read -- with $ICF_2CF_2Br$ --.

Column 7, line 34, "consisting aryl," should read -- consisting of aryl, --.

Column 7, line 47, "selected form the group" should read -- selected from the group --.

Column 7, line 62, "metal salt or an alcohol" should read -- metal salt of an alcohol --.

Signed and Sealed this

Second Day of October 1984

[SEAL]

Attest:

Attesting Officer

GERALD J. MOSSINGHOFF

Commissioner of Patents and Trademarks